United States Patent
Hiltner et al.

(10) Patent No.: US 7,436,499 B2
(45) Date of Patent: Oct. 14, 2008

(54) PLASTIC PACKAGING HAVING A MARKER MATERIAL

(75) Inventors: James Hiltner, Sylvania, OH (US); Michael Hsieh, San Jose, CA (US)

(73) Assignee: Rexam Healthcare Packaging Inc., Perrysburg, OH (US)

( * ) Notice: Subject to any disclaimer, the term of this patent is extended or adjusted under 35 U.S.C. 154(b) by 10 days.

(21) Appl. No.: 11/199,731

(22) Filed: Aug. 9, 2005

(65) Prior Publication Data

US 2007/0035719 A1   Feb. 15, 2007

(51) Int. Cl.
*G06K 9/74* (2006.01)

(52) U.S. Cl. .................. 356/71; 356/71; 250/338.1; 250/339.01; 428/913

(58) Field of Classification Search ............. 356/71; 250/338.1, 339.01–339.12; 428/913
See application file for complete search history.

(56) References Cited

U.S. PATENT DOCUMENTS

| | | | |
|---|---|---|---|
| 4,261,473 A | 4/1981 | Yamada et al. | |
| 4,299,330 A * | 11/1981 | Walter | 220/288 |
| 4,491,598 A * | 1/1985 | Hsu et al. | 426/127 |
| 5,347,111 A | 9/1994 | Hoshino | |
| 5,591,527 A | 1/1997 | Lu | |
| 5,743,981 A | 4/1998 | Lu | |
| 6,297,508 B1 * | 10/2001 | Barmore et al. | 250/459.1 |
| 6,608,116 B2 | 8/2003 | Symons et al. | |
| 6,628,439 B2 | 9/2003 | Shiozawa et al. | |
| 6,806,478 B1 * | 10/2004 | Hatfield | 250/472.1 |
| 2002/0010225 A1 | 1/2002 | Symons et al. | |
| 2002/0051264 A1 | 5/2002 | Shiozawa et al. | |
| 2002/0130186 A1 | 9/2002 | Lasch et al. | |
| 2003/0065938 A1 | 4/2003 | Kitamura et al. | |
| 2003/0112423 A1 * | 6/2003 | Vig et al. | 356/71 |
| 2003/0203140 A1 | 10/2003 | Sapatova et al. | |

FOREIGN PATENT DOCUMENTS

| | | | |
|---|---|---|---|
| EP | 0990890 | | 4/2000 |
| WO | WO 97/21186 | * | 6/1997 |
| WO | WO 9721186 | * | 6/1997 |

* cited by examiner

*Primary Examiner*—L. G. Lauchman
*Assistant Examiner*—Iyabo S Alli
(74) *Attorney, Agent, or Firm*—Reising, Ethington, Barnes, Kisselle, P.C.

(57) ABSTRACT

A package including a container and closure, and a method of authenticating same. In the package or a portion thereof, a marker material is dispersed into a base material and can be detected in the aftermarket by absorption spectroscopy to establish the authenticity of a product contained in the package.

6 Claims, 2 Drawing Sheets

PLASTIC PACKAGING HAVING A MARKER MATERIAL

The present invention is directed to methods of authenticating products and to plastic packages, and more particularly to plastic packaging including a hollow plastic container and closure having an identifiable security measure therein and to a method of authenticating such packaging to combat use of counterfeit plastic packages.

BACKGROUND AND SUMMARY OF THE INVENTION

In the production of plastic packages including closures and hollow plastic containers, it is common to mold or to extrude a preform, and then to blow mold the preform to achieve the final shape of a container. With some containers, at least a body portion of the container is of multilayer construction, in which one or more intermediate layers form a barrier against gas transmission through the container. Whether of monolayer or multilayer construction, blow molded containers, and closures therefor, are often used for packaging personal care products and medical-type products, such as pharmaceuticals. Unfortunately, however, pharmaceuticals are sometimes counterfeited and packaged in counterfeit packages that look identical to genuine packages used to market genuine pharmaceuticals. Accordingly, such counterfeit packages are used to deceive pharmacists and consumers into buying counterfeit pharmaceuticals.

In accordance with one aspect of the present invention, there is provided a method of authenticating packaging that includes at least two steps. First, at least a portion of a package is provided with a material composed of at least one first plastic material that yields a first predetermined electromagnetic energy absorption spectrum and at least one second plastic material that, when blended with the at least one first plastic material, yields a second predetermined electromagnetic energy absorption spectrum. Second, radiant energy is directed through the at least a portion of the package in accordance with at least one electromagnetic energy wavelength associated with the second predetermined absorption spectrum to detect presence or absence of the second material.

In accordance with a second aspect of the invention, a package is provided that includes at least a portion (e.g., a closure or a container) that is composed essentially of at least one first plastic material that yields a first predetermined electromagnetic energy absorption spectrum and at least one second plastic material that, when blended with the at least one first plastic material, yields a second predetermine electromagnetic energy absorption spectrum. The at least one second plastic material is provided in an amount insufficient to substantially affect functional characteristics of the at least one first material, but in amount sufficient for detection by spectroscopy to verify or refute authenticity of the package.

In the preferred embodiments of the invention, intermediate layer(s) of the package are of barrier resin polymer to retard migration of gases, water vapor and/or flavorants through the package wall. However, as will be described, the intermediate layer resin can be of any suitable type, including post consumer resin or the same resin as the matrix resin layer(s). In accordance with this aspect of the invention, a material marker is dispersed in the intermediate resin layer(s) to identify the package. This preferably is accomplished by blending the material marker in the resin prior to or during molding or extruding a preform from which the package is made. In the preferred embodiments of the invention, the material marker is EVA and the base material is HDPE or PP.

A method of verifying authenticity of a package in accordance with another aspect of the invention includes providing in said package at least one packaging component (e.g., a container and/or a closure) that is composed primarily of at least one first plastic material having a first predetermined electromagnetic energy absorption spectrum and has dispersed therein visually non-detectable amounts of a second material having a second electromagnetic energy absorption spectrum different from said first spectrum. Electromagnetic energy is directed onto said packaging component at least one wavelength associated with second energy absorption spectrum to detect presence of said second material dispersed in said first material. A packaging component (e.g., a closure or container) is composed essentially of at least one first plastic material that has a first electromagnetic energy absorption spectrum and at least one second plastic material that has a second electromagnetic energy absorption spectrum different from said first spectrum, said at least one second material be in an amount insufficient to affect functional characteristics of said at least one first material, but in an amount sufficient for detection by absorption spectroscopy to confirm authenticity of said component.

BRIEF DESCRIPTION OF THE DRAWINGS

The invention, together with additional objects, features, advantages and aspects thereof, will be best understood from the following description, the appended claims and the accompanying drawings, in which:

DETAILED DESCRIPTION OF PREFERRED EMBODIMENTS

Figure 1:
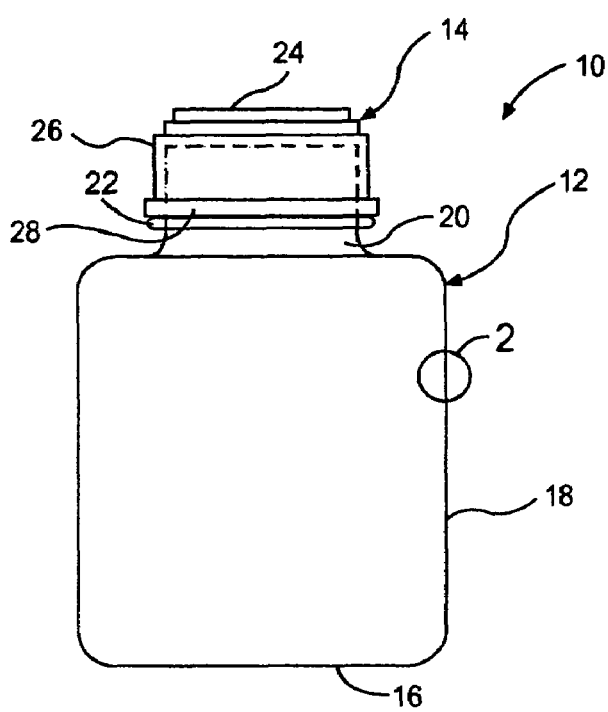
FIG. 1 is a side elevational view of a plastic package including a container and a closure according to one exemplary embodiment of the present invention.

In general reference to FIG. 1, there is illustrated an "authentic" plastic package 10 in accordance with an exemplary embodiment of the present invention. As used herein, the term "authentic" means having a claimed, verifiable origin and not counterfeit or copied. The package 10 is assembled from individual plastic packaging components including an authentic plastic container 12 for packing one or more authentic products therein such as authentic pharmaceutical pills or the like, and an authentic closure 14 for sealingly retaining the products within the container 12 to create an authentic packaged product. The authentic packaged product is thereafter distributed into a market such as a wholesale, distributor, and/or consumer market. In such a market or in the aftermarket it may be desirable to confirm or refute the authenticity of a package and/or the authenticity of products within the package via the authenticity of the package. Accordingly, one desiring to establish authenticity first obtains a packaged product that is either an authentic packaged product or is a counterfeit packaged product that resembles the authentic packaged product, then performs a material analysis of the packaged product in accordance with techniques described herein below.

In more specific reference to FIG. 1, the container 12 includes a closed bottom end 16, a sidewall 18 extending away from the closed bottom end 16, and a neck finish portion 20 terminating the sidewall 18, including a support flange 22, and ultimately terminating in an open end (not shown) substantially opposite of the closed bottom end 16. The container 12 may be produced by any known method of forming containers, but preferably is produced by blow molding an injection-molded, compression-molded or extrusion-formed preform (not shown) from one or more base materials and one or more marker materials blended or dispersed in the base material(s). The closure 14 includes a base wall 24 from which depends an annular skirt wall 26 that terminates in an open end 28 that is substantially opposite of the base wall 24. The closure 14 preferably attaches to the container 12 via a threaded connection by external threads (not shown) on the neck finish 20 of the container 12 that interengage internal threads (not shown) projecting inwardly from the skirt wall 26 of the closure 14. Snap-bead attachment also may be employed. Snap-bead engagement alternatively can be employed.

Figure 2:
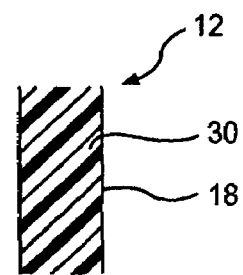
FIG. 2 illustrates an enlarged, fragmentary cross-sectional view of a sidewall of the container of FIG. 1, taken from circle 2 thereof.
Figure 3:
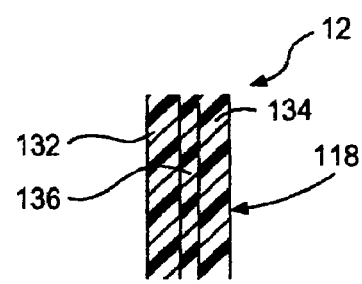
FIG. 3 illustrates an embodiment alternative to that of FIG. 2, illustrating a multi-layer sidewall.

FIG. 2 depicts an enlarged cross-sectional portion of the container 12 of FIG. 1 taken from circle 2 thereof. FIG. 2 may also be representative of a cross-sectional wall portion of the closure 14 of FIG. 1. The wall 18 is of monolayer construction, having a single layer 30 composed of a first plastic material, or base material, and a second plastic material, or additive, which is blended with the first plastic material and provided in a visually non-detectable amount. The terminology "visually non-detectable amount" means that the amount of the second material is so low as to be unnoticeable to the naked human eye. The first plastic material yields, or may be characterized by, a first predetermined electromagnetic energy absorption spectrum under spectroscopy techniques, and may be composed of any desired resin such as a matrix resin, barrier resin, or a blend thereof. Preferably, the first material is composed of high density polyethylene (HDPE) or polypropylene (PP), but may be composed of any desired packaging material. The second plastic material, when blended with the first, yields or may be characterized by, a second predetermined electromagnetic energy absorption spectrum, and may be composed of any desired marker material. The marker material is provided in an amount that is not visible to a naked human eye and is insufficient to substantially affect the functional characteristics of the base material. Accordingly, a potential counterfeiter cannot readily ascertain the presence of the marker material in an authentic packaged product. The marker material is preferably ethylene vinyl acetate (EVA) in an amount on the order of three to five weight percent of the total material. It is however, contemplated that more or less EVA could be used to mark the packaging. EVA is preferred because it is readily available and inexpensive.

FIG. 2A depicts an enlarged cross-sectional portion of a container (or closure) 112 according to an alternative embodiment of the present invention. Here, it is preferred that a wall 118 be multilayered, preferably from multiple molten resins, and includes inside and outside layers 132, 134, and an intermediate layer 136. As with the embodiment of FIG. 2, one or more of the layers 132, 134, 136 is composed of a first plastic material having a first predetermined energy absorption spectrum and a second plastic material having a second predetermined energy absorption spectrum, such as a marker material composed of EVA in an amount on the order of about three to five percent of the total composition of the particular layer in which the EVA is blended.

The inside and outside layer 132, 134 are composed of a matrix resin polymer and the intermediate layer 136 is composed of a barrier resin polymer. The barrier resin polymer is provided to retard migration of gases, water vapor and/or flavorants through the container sidewall 118. It is contemplated that the multilayered sidewall 118 could be composed of more or fewer layers without departing from the scope of the invention. The multilayer container 112, and the preform from which it is produced, preferably have N matrix layers (e.g., two or three) and N−1 intermediate layers (e.g., one or two). In any case, the matrix resin layers 132, 134 are preferably composed of HDPE or PP, but may be composed of any other desired container material including but not limited to polyethylene terephthalate (PET) or polycarbonate (PC) polymer. The intermediate layer 136 is preferably composed of a nylon or ethylene vinyl alcohol (EVOH) passive polymer, but may be composed of any other suitable passive or active barrier polymer used for containers. However, the intermediate layer 136 could also be of PET or polycarbonate composition, or of post consumer resin composition, in accordance with the broadest aspects of the invention inasmuch as it is the EVA blended in one or more of the layers 132, 134, 136 that provides one of the distinguishing features of the invention.

Figure 4:
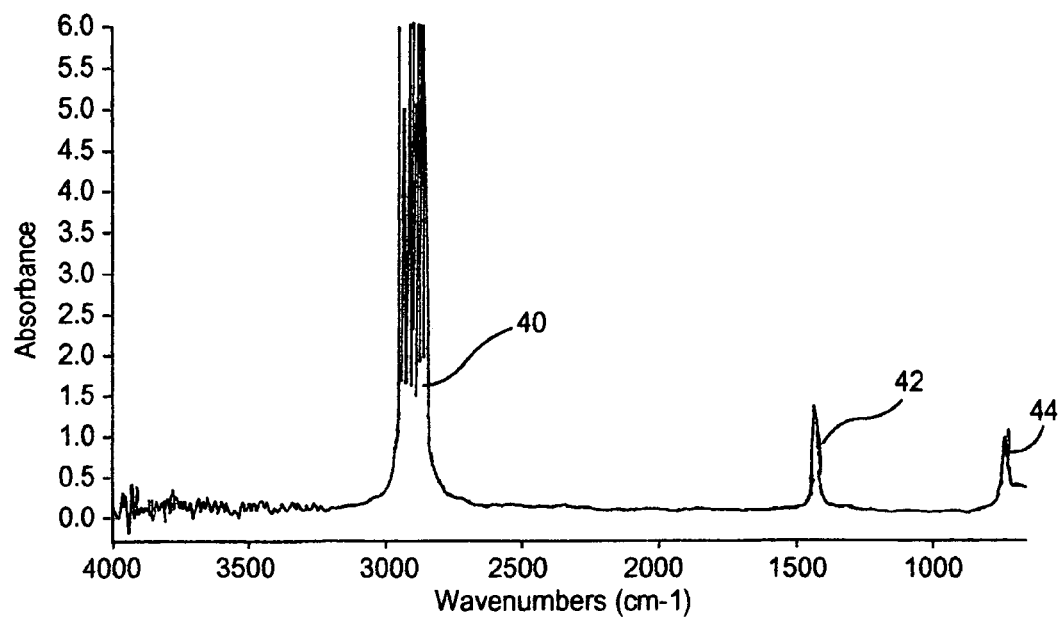
FIG. 4 illustrates a graph of an absorption spectrum displaying the absorption of infrared radiation, as a function of wavelength, through a sample package composed of a first base material.

FIG. 4 illustrates an infrared energy absorption spectrum of the first material without the second material (EVA marker). In general, an absorption spectrum is a plot of an intensity of radiation (along the ordinate) as a function of wavelength of the radiation (along the abscissa) and is used to provide a basis for the determination of qualitative and quantitative chemical composition analyses. Material molecules absorb energy at particular wavelengths of the energy in a known characteristic manner. Thus, it is possible to determine material composition by spectroscopically analyzing the emission or absorption characteristics of the material.

In general, an electromagnetic energy absorption spectrum may be produced by spectroscopy techniques using any of a variety of instruments such as spectroscopes, spectrographs, spectrometers, spectrophotometer, and interferometers. Specifically, an absorption spectrum is typically produced by interposing a thin film of a sample material between a source of radiation and a background. A known continuous spectrum of radiant energies is produced by collimating and separating the source radiation into its components. This spectrum of radiant energies is passed through the sample material and the result is detected in the background. The sample material acts as an absorbing medium to reduce the intensity of the radiation at certain wavelengths, thereby modifying the background. The energies removed from the background by the interposed absorbing medium are those that would be emitted by the absorbing medium if the medium were properly excited and, thus, are indicative of the chemical composition of the medium. Accordingly, the difference in energy between the applied radiation spectrum and the transmitted, but not absorbed, energies that form the background spectrum are measured to infer the chemical composition of the sample material. The spectroscopic analysis may be destructive or non-destructive.

Referring still to FIG. 4, Fourier transform infrared (FTIR) spectroscopy was used to develop the absorption spectrum, wherein a radiation source was used to simultaneously apply all pertinent wavelengths to irradiate the sample material for a relatively short period and the absorption spectrum was thereafter obtained by Fourier mathematical manipulation. The spectrum was generated using film transmission analysis with a Nicolet 510 spectrometer having a DTGS KBr detector, a KBr beamsplitter, and an infrared source. The spectrometer settings include 32 sample and background scans, 4.000 resolution, 32.0 sample gain, 1.5825 mirror velocity, and a 30.00 aperture.

FIG. 4 illustrates the absorption spectrum of HDPE with 0% EVA, wherein primary, secondary, and tertiary spikes 40, 42, 44 in absorbance are readily apparent. The primary spike 40 occurs at a wavelength of about 2900 $cm^{-1}$, the secondary spike 42 occurs at about 1450 $cm^{-1}$, and the tertiary spike occurs at about 700 $cm^{-1}$. These wavelength spikes are characteristic of HDPE and thereby positively identify the 100% HDPE base material.

Figure 5:
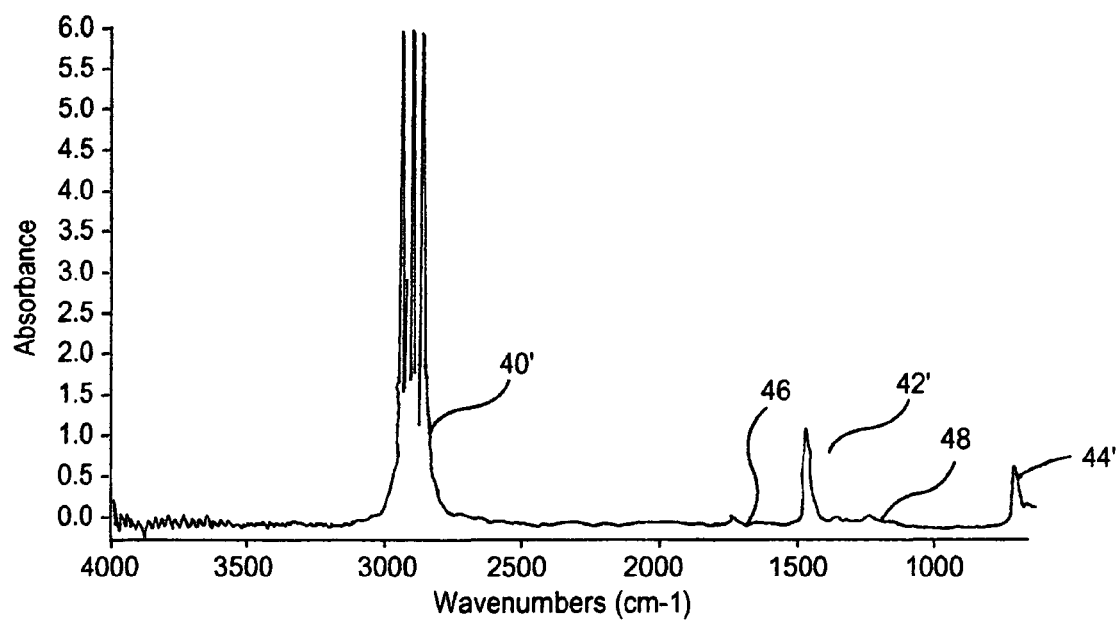
FIG. 5 illustrates a graph of an absorption spectrum displaying the absorption of infrared radiation through another sample package composed of the first material and a second marker material.

FIG. 5 illustrates the absorption spectrum of HDPE that is blended with 5% EVA. The same equipment and settings were used to generate this spectrum, except that 64 sample and background scans were used instead of 32. As one would expect, the HDPE spikes of FIG. 4 are basically unchanged in this spectrum because HDPE is still present in an amount on the order of about 95% of the total material composition, i.e. predominantly the same as with the material associated with FIG. 4. But it is apparent that this reduced HDPE content has resulted in some change in the spectrum, yielding somewhat less dense or intense primary, secondary, and tertiary spikes 40', 42', 44'. It is also apparent that the addition of the EVA content has resulted in other changes in the spectrum, yielding EVA primary and secondary spikes 46, 48 at 1741 $cm^{-1}$ and 1241 $cm^{-1}$ respectively. These additional wavelength spikes are characteristic of EVA and thereby positively identify the presence of the EVA material.

With one or more of the exemplary embodiments discussed above, an authentic or "genuine" package, container and/or closure of the present invention including a marker material can be more readily distinguished from a counterfeit or non-genuine container not bearing such a marker material. A particular material signature can be associated with a particular legitimate origin or source such as a container manufacturer, a particular product or pharmaceutical, a manufacturer, a factory or production facility, a marketer, a distributor, a retailer, a pharmacist, or the like. By inspecting a portion of the packaging, such as with spectroscopy techniques, the marker material may be identified, and a product and/or its packaging can thereby be verified as authentic in a given market or aftermarket, wherein the packaging can be reliably traced back to a particular desired origin or source. In other words, if there is any question about the legitimacy of the packaging or product therein, the marker material provides traceable proof of origin of the packaging. In essence, the present invention provides a material signature for identifying the authenticity of packaging or products that is a reliable packaging security feature against counterfeiting of the packaging or products contained therein and, therefore, the marked package is difficult for counterfeiters to reproduce. Thus, by using the present invention, pharmacists and consumers are relatively more protected against the intrusion of counterfeit pharmaceuticals into the marketplace.

There have thus been described a package, container, closure, and a method of verifying authenticity of same that fully satisfy all of the objects and aims previously set forth. The present invention has been disclosed in conjunction with presently preferred embodiments thereof, and a number of modifications and variations have been discussed. Other modifications and variations will readily suggest themselves to persons of ordinary skill in the art in view of the foregoing description. For example, different spectroscopy techniques and different spectrums can be used such as emission spectroscopy and spectrums. Such techniques and spectrums are equivalent to that disclosed herein because they function in substantially the same manner to provide substantially similar results. Finally, directional words such as top, bottom, upper, lower, radial, circumferential, and the like are employed by way of description and not limitation. Indeed, the invention is intended to embrace all modifications and variations as fall within the spirit and broad scope of the appended claims.

The invention claimed is:

1. A package that includes:
    a plastic container having a closed bottom end, a sidewall extending away from said closed bottom end and a neck finish extending from said sidewall, and
    a plastic closure having a skirt externally removably threaded onto said neck finish,
    at least one of said closure or said container including a blend of plastic resins comprising a base resin having a first infrared absorption spectrum, and a marker resin that is visually non-detectable in said base resin and having a second infrared absorption spectrum different from said first spectrum,
    presence of said marker resin being detectable by infrared absorption spectroscopy to confirm genuineness of said package.

2. The package set forth in claim 1 wherein said marker resin is EVA.

3. The package set forth in claim 2 wherein said base resin is HDPE or PE.

4. The package set forth in claim 1 wherein said marker resin is disposed in a portion of said closure or said container that is of monolayer construction.

5. The package set forth in claim 1 wherein said marker resin is disposed in a portion of said closure or said container that is of multilayer construction.

6. The package set forth in claim 1 wherein said marker resin is in the amount of about three percent to five percent of said blend.

* * * * *